(12) United States Patent
Liu et al.

(10) Patent No.: US 8,141,767 B2
(45) Date of Patent: Mar. 27, 2012

(54) METHOD FOR MAKING TRANSMISSION ELECTRON MICROSCOPE MICRO-GRID

(75) Inventors: Liang Liu, Beijing (CN); Li Fan, Beijing (CN); Chen Feng, Beijing (CN); Li Qian, Beijing (CN); Yu-Quan Wang, Beijing (CN)

(73) Assignee: Beijing FUNATE Innovation Technology Co., Ltd., Beijing (CN)

( * ) Notice: Subject to any disclaimer, the term of this patent is extended or adjusted under 35 U.S.C. 154(b) by 0 days.

(21) Appl. No.: 12/944,165

(22) Filed: Nov. 11, 2010

(65) Prior Publication Data

US 2011/0253300 A1   Oct. 20, 2011

(30) Foreign Application Priority Data

Apr. 14, 2010   (CN) .......................... 2010 1 0146386

(51) Int. Cl.
*B23K 31/02* (2006.01)
(52) U.S. Cl. ....................................... 228/101; 228/136
(58) Field of Classification Search ........................ None
See application file for complete search history.

(56) References Cited

U.S. PATENT DOCUMENTS

| 7,745,302 B2 * | 6/2010 | Zhang et al. | 438/409 |
| 2008/0237464 A1 * | 10/2008 | Zhang et al. | 250/311 |
| 2009/0317926 A1 | 12/2009 | Zhang et al. | |
| 2010/0181482 A1 * | 7/2010 | Zhang et al. | 250/311 |
| 2011/0192987 A1 * | 8/2011 | Qian et al. | 250/440.11 |
| 2011/0192988 A1 * | 8/2011 | Feng et al. | 250/440.11 |

FOREIGN PATENT DOCUMENTS

| CN | 101276724 A | | 10/2008 |
| CN | 101609771 | | 12/2009 |
| JP | 2006-244742 A | * | 9/2006 |
| JP | P2006-244742 A | | 9/2006 |
| JP | 2008-027763 A | * | 2/2008 |
| JP | 2008-235192 A | * | 10/2008 |

* cited by examiner

*Primary Examiner* — Kiley Stoner
(74) *Attorney, Agent, or Firm* — Altis Law Group, Inc.

(57) ABSTRACT

A method for making a TEM micro-grid is provided. The method includes the following steps. A carrier, a carbon nanotube structure, and a protector are provided. The carrier defines a first through opening. The protector defines a second through opening. The protector, the carbon nanotube structure and the carrier are stacked such that the carbon nanotube structure is located between the carrier and the protector. The second through opening at least partly overlaps with the first through opening. The carrier and the protector are welded with each other.

20 Claims, 15 Drawing Sheets

METHOD FOR MAKING TRANSMISSION ELECTRON MICROSCOPE MICRO-GRID

RELATED APPLICATIONS

This application claims all benefits accruing under 35 U.S.C. §119 from China Patent Application No. 201010146386.9, filed on Apr. 14, 2010 in the China Intellectual Property Office, the disclosure of which is incorporated herein by reference. This application is related to applications entitled "TRANSMISSION ELECTRON MICROSCOPE MICRO-GRID", filed Nov. 11, 2010 (Ser. No. 12/944,158); "TRANSMISSION ELECTRON MICROSCOPE MICRO-GRID", filed Nov. 11, 2010 (Ser. No. 12/944,169); "METHOD FOR MAKING TRANSMISSION ELECTRON MICROSCOPE MICRO-GRID", filed Nov. 11, 2010 (Ser. No. 12/944,176) and "METHOD FOR MANUFACTURING TRANSMISSION ELECTRON MICROSCOPE MICRO-GRID", filed Nov. 11, 2010 (Ser. No. 12/944,191).

BACKGROUND

1. Technical Field

The present disclosure relates to methods for making transmission electron microscope (TEM) micro-grids and, in particular, to a method for making a TEM micro-grid based on carbon nanotubes.

2. Discussion of Related Art

In a transmission electron microscope, a porous carbon supporting film (i.e., micro-grid) is used to carry powder samples to observe high resolution transmission electron microscopy images. With the development of nanotechnology, micro-grids are increasingly coming into widespread use in the field of electron microscopy. The micro-grids used in TEMs are usually manufactured using a layer of organic porous membrane covered on a metal mesh net, such as a copper mesh net or a nickel mesh net, and subsequently a layer of non-crystal carbon films are deposited thereon by evaporation.

Carbon nanotubes have special structures and excellent properties, and can form a carbon nanotube structure. The carbon nanotube structure can be used in the TEM micro-grids to reduce the interference non-crystal carbon films have on samples. However, the weight of the carbon nanotubes are light, therefore, the carbon nanotube structure is also light. If the carbon nanotube structure is used in the TEM micro-grids, the carbon nanotube structure floats, thereby affecting resolution transmission of the electron microscopy images and accuracy of measurement.

What is needed, therefore, is to provide a method for making a TEM micro-grid which can prevent the carbon nanotube structure from floating when the micro-grid is used in TEM.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
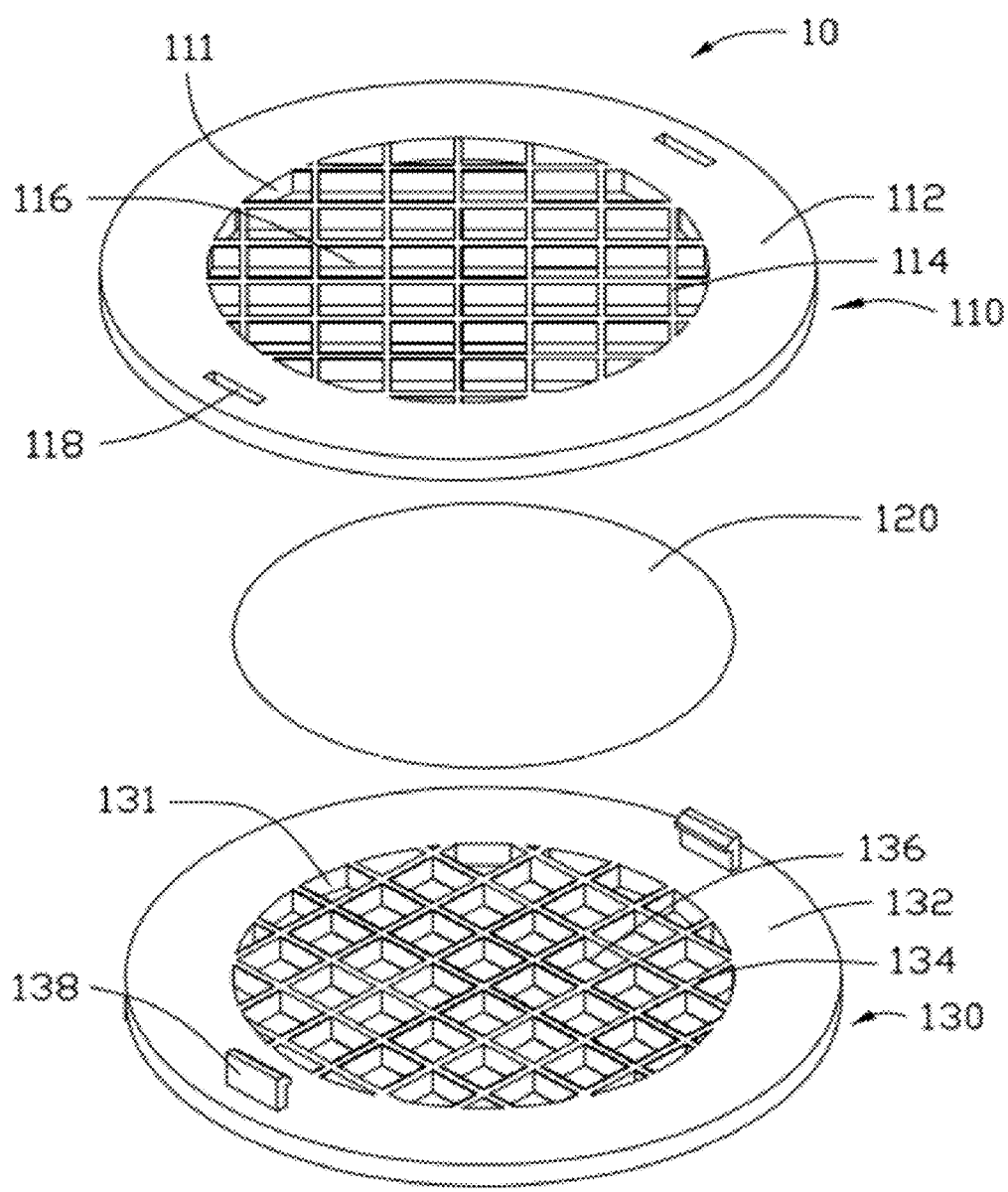
FIG. 1 is an exploded, isometric view of one embodiment of a TEM micro-grid.
Figure 2:
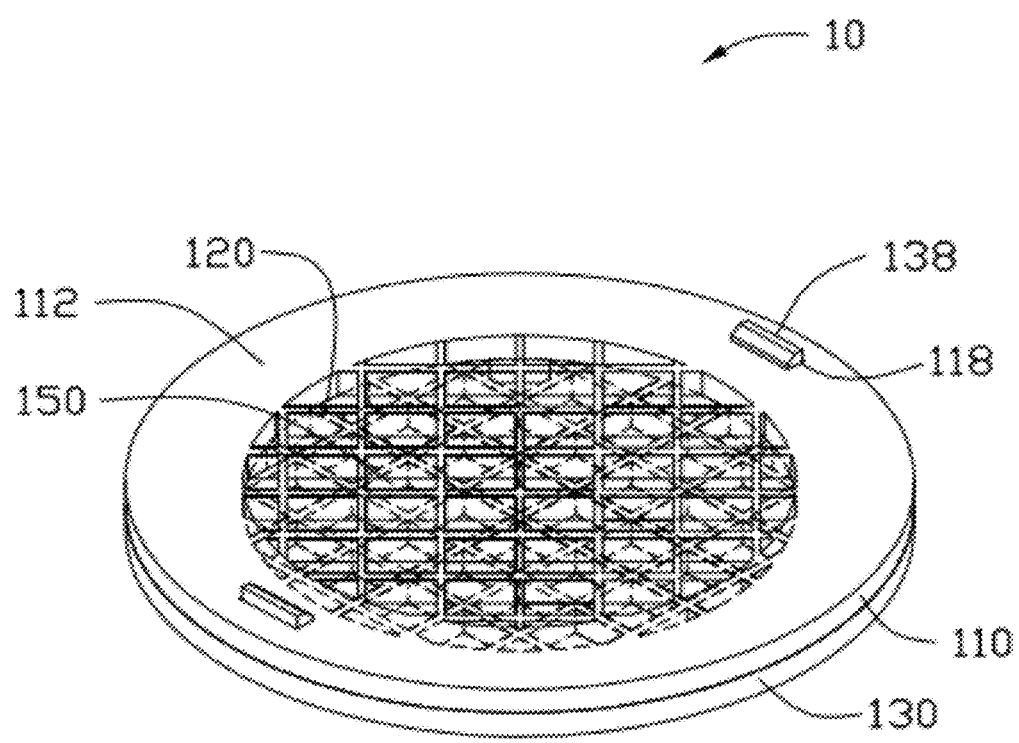
FIG. 2 is an assembled isometric view of the micro-grid of FIG. 1.

Referring to FIG. 1 and FIG. 2, one embodiment of a TEM micro-grid 10 includes a carrier 110, a carbon nanotube supporter 120, and a protector 130. The carbon nanotube supporter 120 is located between the carrier 110 and the protector 130. In one embodiment, the TEM micro-grid 10 is substantially round sheet shape. The diameter of the TEM micro-grid 10 is about 3 millimeters (mm), and the thickness of the TEM micro-grid 10 is from about 3 micrometers (μm) to about 20 μm.

The carrier 110 is used to support the carbon nanotube supporter 120. A material of the carrier 110 can be copper, nickel, molybdenum, or ceramic. In one embodiment, the carrier 110 can be a sheet-shaped structure. The carrier 110 includes a first round frame 112. The first round frame 112 defines a first through opening 111 at a center. A plurality of crossed bars (not labeled) is formed in the first through opening 111 to divide the first through opening 111 into a plurality of first through holes 116. The crossed bars and the first through holes 116 cooperatively define a first net 114. In one embodiment, the through opening has a circular configuration. A shape of each of the first through holes 116 can be round, quadrangle, hexagon, octagon, ellipse, or other shapes. A maximum width of each of the plurality of first through holes 116 can be selected as desired, such as in a range from about 10 μm to about 200 μm. The plurality of first through holes 116 can be arranged as desired. The distance between two adjacent first through holes 116 can be greater than 1 μm. The first net 114 can be formed by an etching method.

In one embodiment, a maximum diameter of the carrier 110 is about 3 mm, the material of the carrier 110 is copper, and a bottom surface of the first net 114 and a bottom surface of the first round frame 112 are substantially coplanar. The first round frame 112 further defines two slits 118. The two slits 118 allow the protector 130 to be tightly fixed on the carrier 110. Each of the through holes 116 is rectangular and uniformly arranged in the carrier 110 to form an array. The space between two adjacent first through holes 116 is substantially identical. The maximum width of the first through hole 116 is from about 40 μm to about 120 μm.

The carbon nanotube supporter 120 is located on the bottom surface of the carrier 110, and covers at least one part of the first through holes 116. The carbon nanotube supporter 120 can be a sheet-shaped structure. In one embodiment, the carbon nanotube supporter 120 covers all of the first through holes 116. The carbon nanotube supporter 120 is a round sheet-shaped structure with a diameter of less than or equal to 3 mm. The diameter of the carbon nanotube supporter 120 can be less than or equal to 2.8 mm. In one embodiment, the diameter of the carbon nanotube supporter 120 is about 2.6 mm. A thickness of the carbon nanotube supporter 120 can be less than 100 μm.

Figure 3:
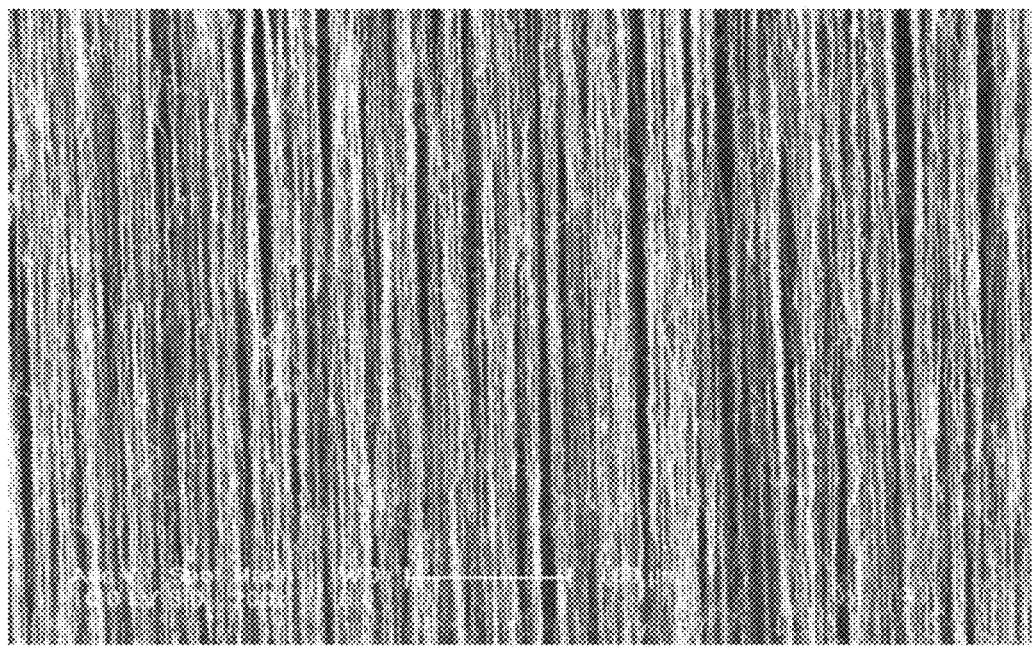
FIG. 3 shows a Scanning Electron Microscope image of a carbon nanotube film.

The carbon nanotube supporter 120 can be a carbon nanotube structure. The carbon nanotube structure includes at least one carbon nanotube film. A carbon nanotube film shown in FIG. 3 includes a plurality of carbon nanotubes that can be arranged substantially parallel to a surface of the carbon nanotube film. A large number of the carbon nanotubes in the carbon nanotube film can be oriented along a preferred orientation, meaning that a large number of the carbon nanotubes in the carbon nanotube film are arranged substantially along the same direction. An end of one carbon nanotube is joined to another end of an adjacent carbon nanotube arranged substantially along the same direction by van der Waals attractive force. A small number of the carbon nanotubes can be randomly arranged in the carbon nanotube film, which has a small if not negligible effect on the larger number of the carbon nanotubes in the carbon nanotube film arranged substantially along the same direction.

The carbon nanotube film is capable of forming a freestanding structure. The term "freestanding structure" can be defined as a structure that does not have to be supported by a substrate. For example, a freestanding structure can sustain its weight when hoisted by a portion thereof without any significant damage to its structural integrity. So, if the carbon nanotube film is placed between two separate supporters, a portion of the carbon nanotube film not in contact with the two supporters would be suspended between the two supporters and still maintain film structural integrity. The freestanding structure of the carbon nanotube film is realized by the successive carbon nanotubes joined end to end by van der Waals attractive force.

It can be appreciated that some variation can occur in the orientation of the carbon nanotubes in the carbon nanotube film. Microscopically, the carbon nanotubes oriented substantially along the same direction may not be perfectly aligned in a straight line, and some curve portions may exist. It can be understood that some carbon nanotubes located substantially side by side and oriented along the same direction may be in contact with each other and cannot be excluded.

More specifically, the carbon nanotube film includes a plurality of successively oriented carbon nanotube segments joined end-to-end by van der Waals attractive force therebetween. Each carbon nanotube segment includes a plurality of carbon nanotubes substantially parallel to each other, and joined by van der Waals attractive force therebetween. The carbon nanotube segments can vary in width, thickness, uniformity, and shape. The carbon nanotubes in the carbon nanotube film are also substantially oriented along a preferred orientation.

In one embodiment, the carbon nanotube structure includes a plurality of carbon nanotube films. Each carbon nanotube film is composed of carbon nanotubes arranged substantially at the same direction. Two adjacent carbon nanotube films are combined by van der Waals attractive force. An angle can be formed between the orientations of carbon nanotubes in the two adjacent carbon nanotube films. The angle can be equal to or greater than 0 degrees, and smaller than or equal to 90 degrees. Examples of the carbon nanotube films are taught by U.S. Pat. No. 7,045,108 to Jiang et al. and US Publication No. 20080248235 to Feng et al. If the angle is greater than 0 degrees and less than or equal to 90 degrees, the orientation of carbon nanotubes in different carbon nanotube films can intercross with each other to form a net structure with a plurality of micropores. The effective diameters of the plurality of micropores relate to the number of layers of the carbon nanotube films. The more the layers of the carbon nanotube films, the smaller the effective diameters of the micropores. The effective diameters of the plurality of micropores can range from about 1 nanometer (nm) to about 1 μm. In one embodiment, the carbon nanotube supporter 120 is composed of two stacked carbon nanotube films. The orientation of the carbon nanotubes in one carbon nanotube film is substantially perpendicular to that in another carbon nanotube film.

In one embodiment, the carbon nanotube structure can include at least one carbon nanotube network. The carbon nanotube network is made by at least one carbon nanotube wire and defines a plurality of micropores. The effective diameters of the micropores can be from about 1 nm to about 1 μm. Each carbon nanotube wire can be composed of carbon nanotubes.

The carbon nanotube wire can be an untwisted carbon nanotube wire or a twisted carbon nanotube wire. An untwisted carbon nanotube wire is formed by treating a carbon nanotube film with an organic solvent. The untwisted carbon nanotube wire includes a plurality of successive carbon nanotubes substantially oriented along an axis of the untwisted carbon nanotube wire and joined end-to-end by van der Waals attraction force therebetween. The untwisted carbon nanotube wire has a diameter ranging from about 0.5 nm to about 1 mm. Examples of an untwisted carbon nanotube wire are taught by U.S. Pat. No. 7,045,108 to Jiang et al. and U.S. Pat. No. 7,704,480 to Jiang et al.

A twisted carbon nanotube wire is formed by twisting a carbon nanotube film by a mechanical force. The twisted carbon nanotube wire includes a plurality of carbon nanotubes oriented around an axis of the twisted carbon nanotube wire. The length of the twisted carbon nanotube wire can be set as desired and the diameter of the carbon nanotube wire can range from about 0.5 nm to about 100 micrometers. The twisted carbon nanotube wire can be treated with an organic solvent before or after twisting.

The protector 130 can be located on a bottom surface of the carbon nanotube supporter 120, and configured to fix the carbon nanotube supporter 120 between the protector 130 and the carrier 110. The structure of the protector 130 can be similar to that of the carrier 110. The protector 130 includes a second round frame 132. The second round frame 132 defines a second through opening 131 at the center. A plurality of crossed bars (not labeled) is formed in the second through opening 131 to divide the second through opening 131 into a plurality of second through holes 136. The crossed bars and the plurality of second through holes 136 cooperatively define a second net 134. The material of the protector 130 can be the same as that of the carrier 110.

In one embodiment, a maximum diameter of the protector 130 is about 3 mm. The material of the protector 130 is copper. A plurality of second through holes 136 is defined in the protector 130. Each second through hole 136 can be rectangle-shaped. The plurality of second through holes 136 is uniformly arranged in the protector 130 to form an array. The protector 130 includes two clasps 138. The two clasps 138 are located on the second round frame 132 and corresponding to the two slits 118. The two clasps 138 can be engaged in the two slits 118 to fix the carrier 110 and the protector 130 to prevent the carbon nanotube supporter 120 from floating when the TEM micro-grid 10 is moved. The plurality of second through holes 136 overlaps with the plurality of first through holes 116, thereby forming a plurality of third through holes 150. The effective diameters of the plurality of third through holes 150 are less than that of the first through holes 116 and the second through holes 136. The effective diameters of the plurality of third through holes 150 are about 20 µm to about 60 µm. Each of the third through holes 150 corresponds to an electron transmission area for supporting samples. The carbon nanotube supporter 120 in each third through hole 150 is suspended.

The slit 118 and the clasp 138 are optional structures, the number of the slits 118 and clasps 138 is not limited to two, and can be one or three or more, to fix the carrier 110 and the protector 130. Furthermore, the carrier 110 and the protector 130 can be fixed tightly by other mechanical methods such as soldering.

As described above, the carbon nanotube supporter 120 is secured between the first round frame 112 and the second round frame 132. The TEM micro-grid 10 can be moved using tweezers to clamp the first round frame 112 and the second round frame 132. The tweezers will not contact the carbon nanotube supporter 120 to prevent contamination by the tweezers. Furthermore, the carbon nanotube supporter 120 has a light weight, thus the carbon nanotube supporter 120 can float easily when the TEM micro-grid 10 is moved. However, if the carbon nanotube supporter 120 is secured between the first round frame 112 and the second round frame 132, the carbon nanotube supporter 120 is prevented from floating when the TEM micro-grid 10 is moved. Therefore, the resolution and accuracy of a TEM adopting the TEM micro-grid 10 can be improved.

In application of the TEM micro-grid 10, the sample to be observed can be laid upon the TEM micro-grid 10. If the sample is larger than the micropores of the carbon nanotube supporter 120, the sample can be placed on a surface of the carbon nanotube supporter 120 and span across at least one of the micropores. If the sample is smaller than the diameter or size of the at least one of the micropores, particularly if the sample is smaller than 5 nm, the sample can be adhered to the walls of the carbon nanotubes of the carbon nanotube supporter 120.

Figure 4:
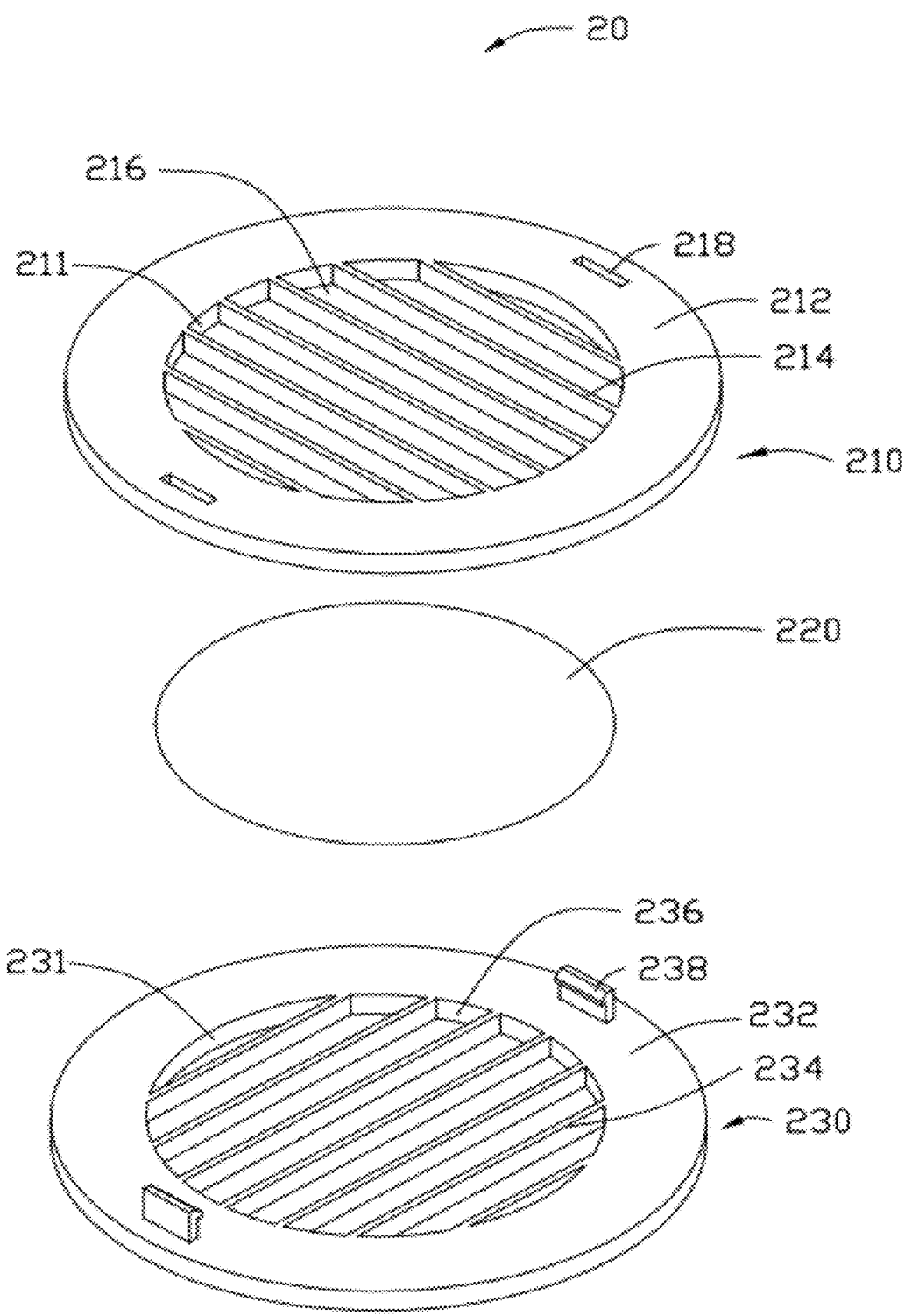
FIG. 4 is an exploded, isometric view of another embodiment of a TEM micro-grid.
Figure 5:
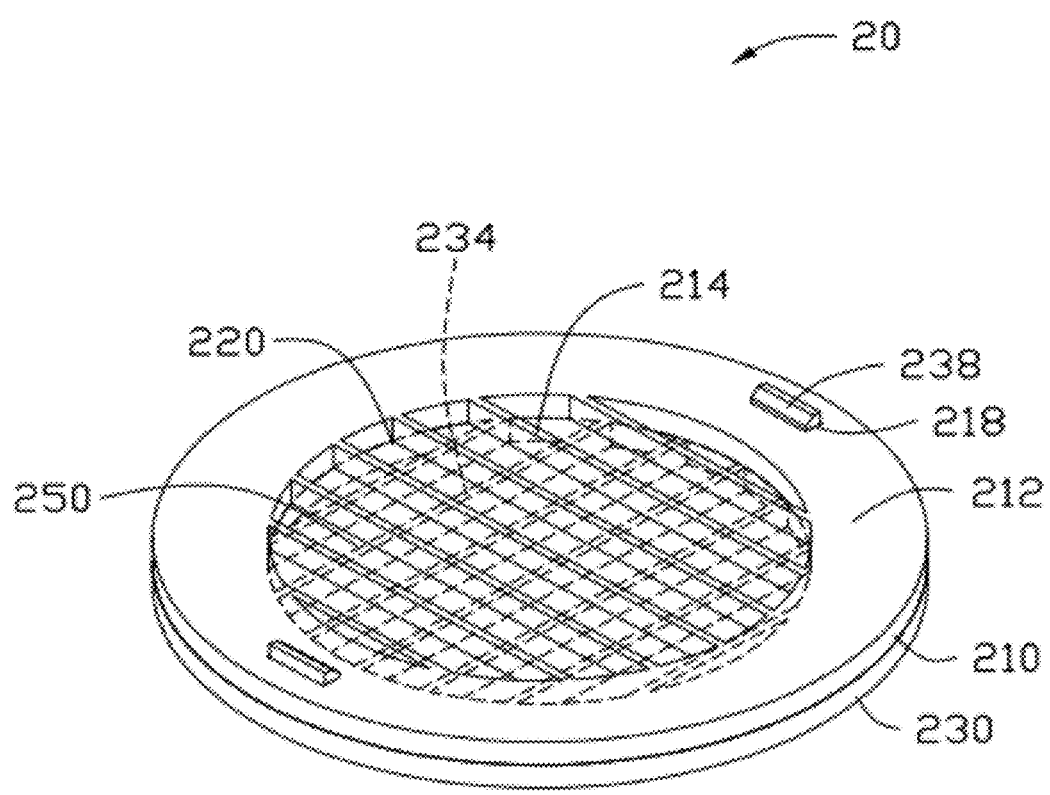
FIG. 5 is a assembled isometric view of the micro-grid of FIG. 4.

Referring to FIG. 4 and FIG. 5, another embodiment of a TEM micro-grid 20 has a substantially round sheet shape. A diameter of the TEM micro-grid 20 can be about 3 mm. A thickness of the TEM micro-grid 20 can be in a range from about 3 µm to about 20 µm. The micro-gird 20 includes a carrier 210, a carbon nanotube supporter 220, and a protector 230.

The carrier 210 can include a first round frame 212 defining two slits 218. The first round frame 212 defines a first through opening 211 at the center. The structure of the carrier 210 is similar to that of the carrier 110 mentioned above, except the carrier 210 can further include a plurality of first bars 214. The plurality of first bars 214 is substantially parallel to each other and separately formed in the first through opening 211 to divide the first through opening 211 into a plurality of first through holes 216. A space of adjacent first through holes 216 can be in an approximate range from 30 µm to 150 µm. The width of each first bar 214 is larger than 1 µm.

The structure of the protector 230 is similar to that of the carrier 210. The protector 230 can include a second round frame 232, a plurality of second bars 234, and two clasps 238. The clasps 238 are located on the second round frame 232 and correspond to the two slits 218, and define a second through opening 231 at the center. The plurality of second bars 234 is substantially parallel to each other and separately located in the second through opening 231. The plurality of bars 234 and the second round frame 232 cooperatively define a plurality of second through holes 236. The plurality of second bars 234 can be substantially perpendicular to the plurality of first bars 214 to define a plurality of third through holes 250. The effective diameter of each third through hole 250 can range from about 30 µm to about 150 µm. The two adjacent third through holes 250 can be spaced from each other. A space of each adjacent third through holes 250 can be larger than 1 µm. The carbon nanotube supporter 220 is suspended over each third through hole 250.

It can be understood that angles can be formed by overlapping the plurality of first bars 214 and the plurality of second bars 234. The angles can be greater than or equal to 0 degrees, and less than or equal to 90 degrees. The arrangements of the first bars 214 and the second bars 234 are not limited. In one embodiment, the first bars 214 can be intercrossed with each other. The space of each adjacent first bars 214 can be about 10 µm to about 200 µm. In one embodiment, the space of each adjacent first bars 214 can be different. The second bars 234 can be intercrossed with each other. The space of each adjacent second bars 234 can be about 10 µm to about 200 µm. In one embodiment, the space of each two adjacent second bars 234 can be different.

It is to be understood that the first bars 214 and the second bars 234 can have different arrangements in the micro-grid 20. The first bars 214 and the second bars 234 can be formed by an etching method or a drawbench.

Figure 6:
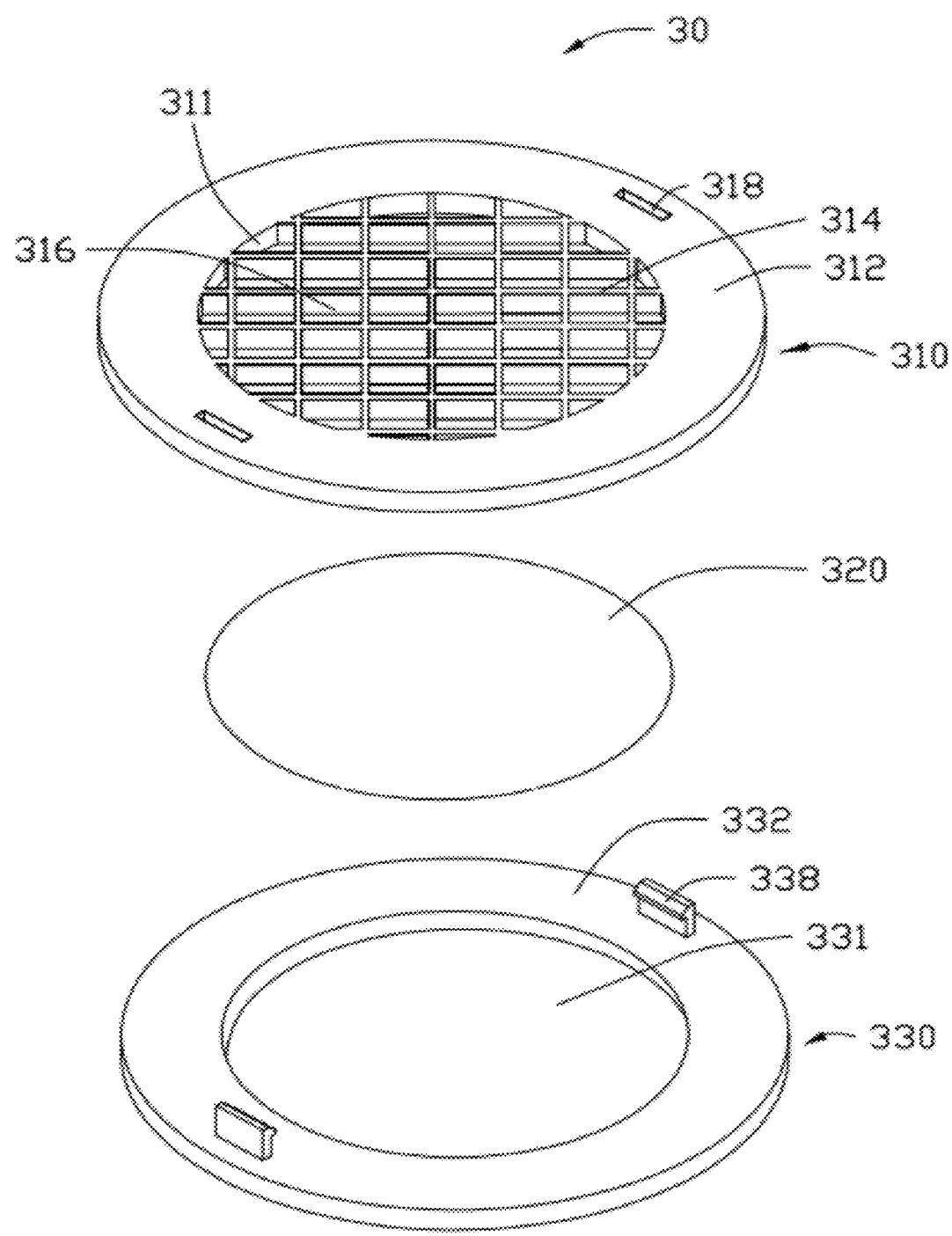
FIG. 6 is an exploded, isometric view of yet another embodiment of a TEM micro-grid.
Figure 7:
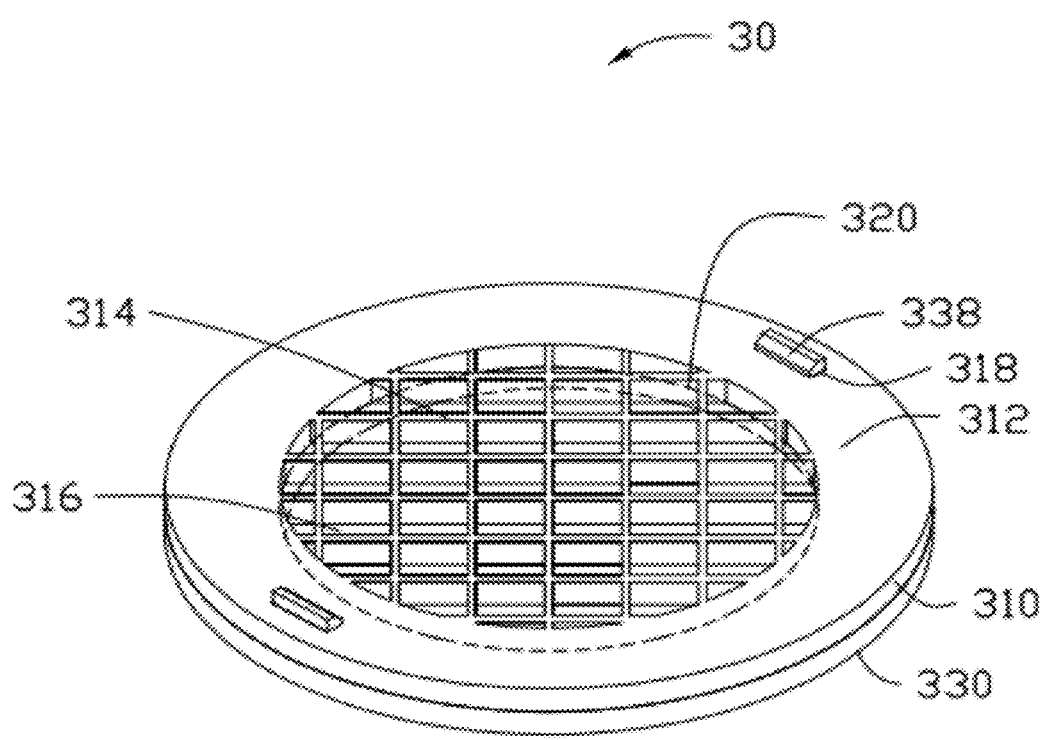
FIG. 7 is an assembled isometric view of the micro-grid of FIG. 6.

Referring to FIG. 6 and FIG. 7, yet another embodiment of a TEM micro-grid 30 includes a carrier 310, a carbon nanotube supporter 320, and a protector 330. The carbon nanotube supporter 320 is located between the carrier 310 and the protector 330.

The carrier 310 can include a first round frame 312. The first round frame 312 defines a first through opening 311 at the center. A plurality of crossed bars (not labeled) is formed in the first through opening 311 to divide the first through opening 311 into a plurality of first through holes 316. The crossed bars and the plurality of first through holes 316 cooperatively define a first net 314. In one embodiment, the through opening has a circular configuration. The protector 330 includes a second round frame 332 and two clasps 338 corresponding to the two slits 318. The two clasps 338 are located on the second round frame 332. The carrier 310 and the protector 330 are fixed tightly by the two slits 318 and the two clasps 338.

The micro-grid 30 is substantially similar to the micro-grid 10 except that the protector 330 is a round ring structure and defines one second through opening 331 at a center without any net or bars. A diameter of the protector 330 is the same as that of the carrier 310. In one embodiment, an inner diameter of the protector 330 is the same as that of the first round frame 312. The first trough hole 316 can correspond to an electron transmission area. The carbon nanotube supporter 320 can be suspended in the electron transmission area.

Figure 8:
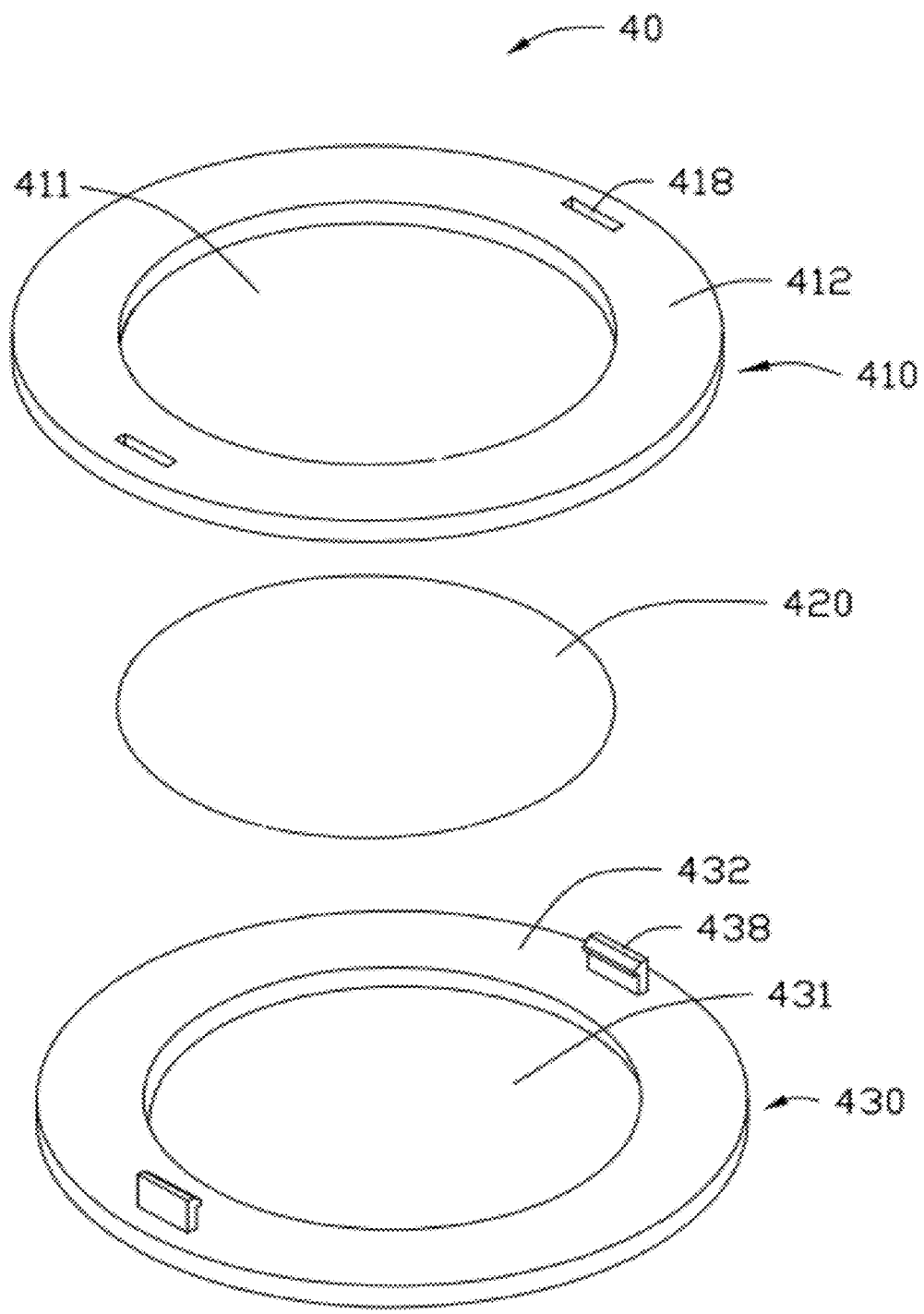
FIG. 8 is an exploded, isometric view of still another embodiment of a TEM micro-grid.
Figure 9:
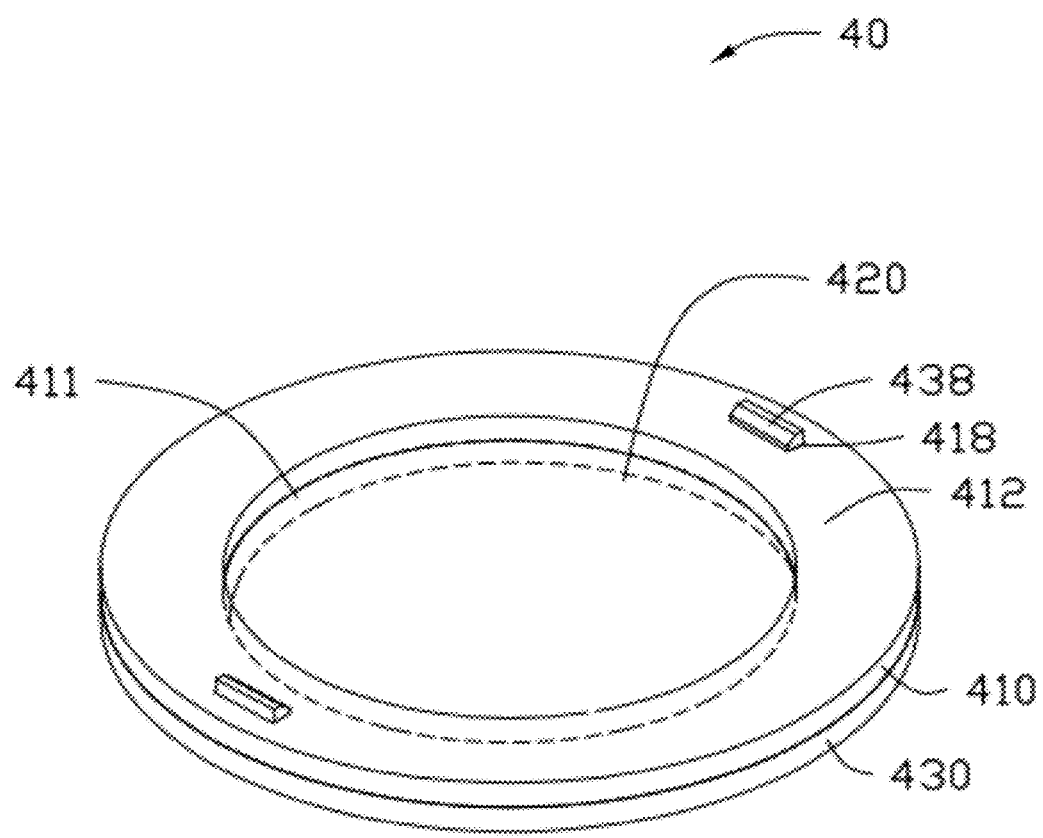
FIG. 9 is an assembled isometric view of the micro-grid of FIG. 8.

Referring to FIG. 8 and FIG. 9, still another embodiment of a TEM micro-grid 40 includes a carrier 410, a carbon nanotube supporter 420, and a protector 430. The micro-grid 40 has a substantially round sheet shape. A diameter of the micro-grid 40 can be about 3 mm. A thickness of the micro-grid 40 can be from about 3 μm to about 20 μm.

Both the carrier 410 and the protector 430 are round ring structures. Specifically, the carrier 410 is a first round ring. The carrier 410 includes a first round frame 412 defining one first through opening 411 at a center and two slits 418. The protector 430 is a round ring. The protector 430 includes a second round frame 432 and two clasps 438. The second round frame 432 defines one second through opening 431 at a center. The two clasps 438 are located on the second round frame 432 and correspond to the two slits 418. Therefore, the carrier 410 and the protector 430 can be fixed by the two clasps 438 engaged in the two slits 418.

The carbon nanotube supporter 420 is fixed between the carrier 410 and the protector 430, and can be suspended in the first through opening 416 and the second through opening 436. A diameter of the carbon nanotube supporter 420 can be slightly larger than inner diameters of the carrier 410 and the protector 430. The carbon nanotube supporter 420 can be the carbon nanotube structure. In one embodiment, the carbon nanotube supporter 420 can be a multi-layer carbon nanotube film with the orientation of carbon nanotubes in each adjacent carbon nanotube film being intercrossed. In another embodiment, the carbon nanotube supporter 420 is a four-layer carbon nanotube film, and the orientations of carbon nanotubes in each adjacent carbon nanotube film are substantially perpendicular to each other. The carbon nanotube supporter 420 can define a plurality of micropores distributed uniformly therein. The effective diameters of the plurality of micropores are about 1 nm to about 0.5 μm.

Figure 10:
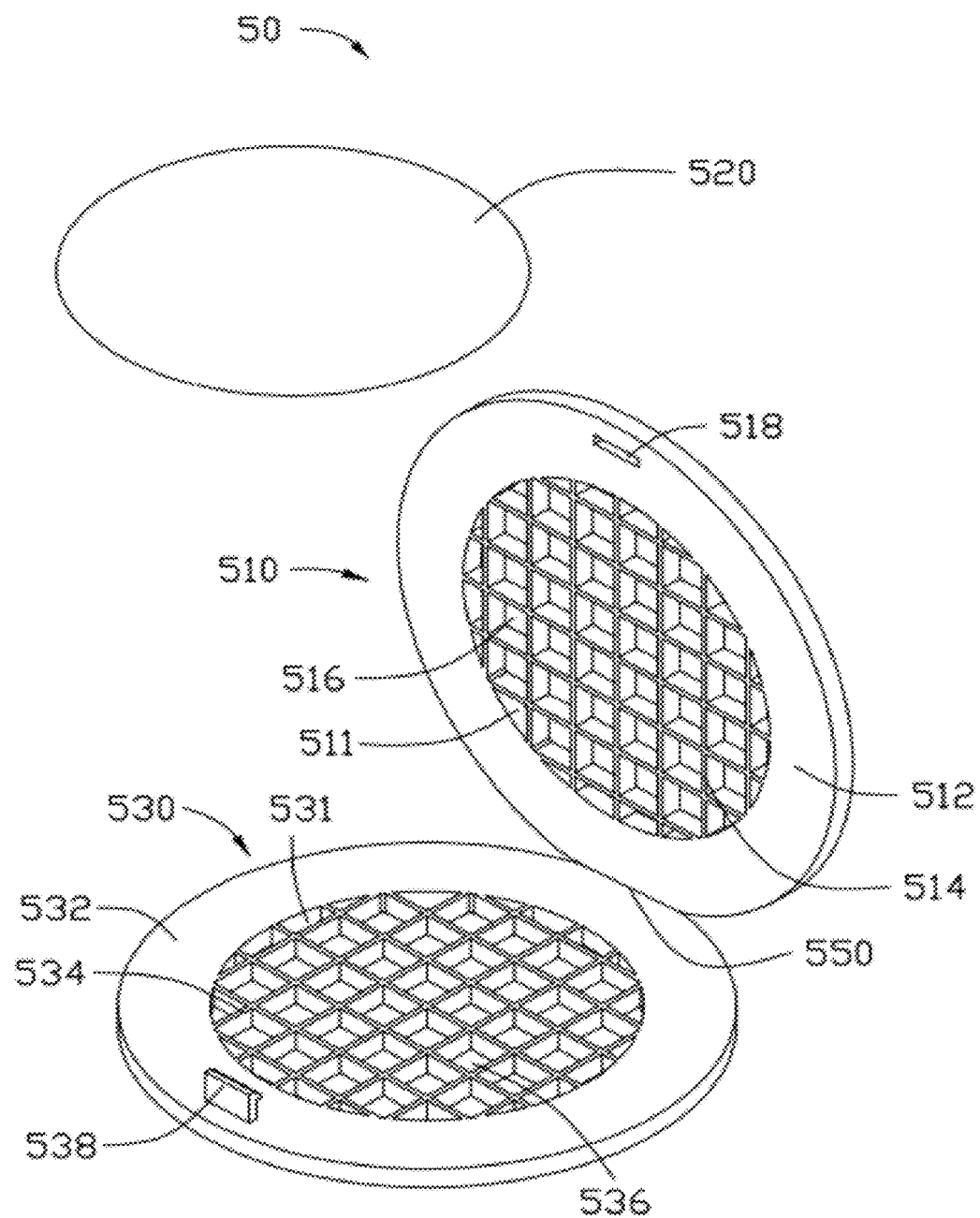
FIG. 10 is an exploded, isometric view of still yet another embodiment of a TEM micro-grid.
Figure 11:
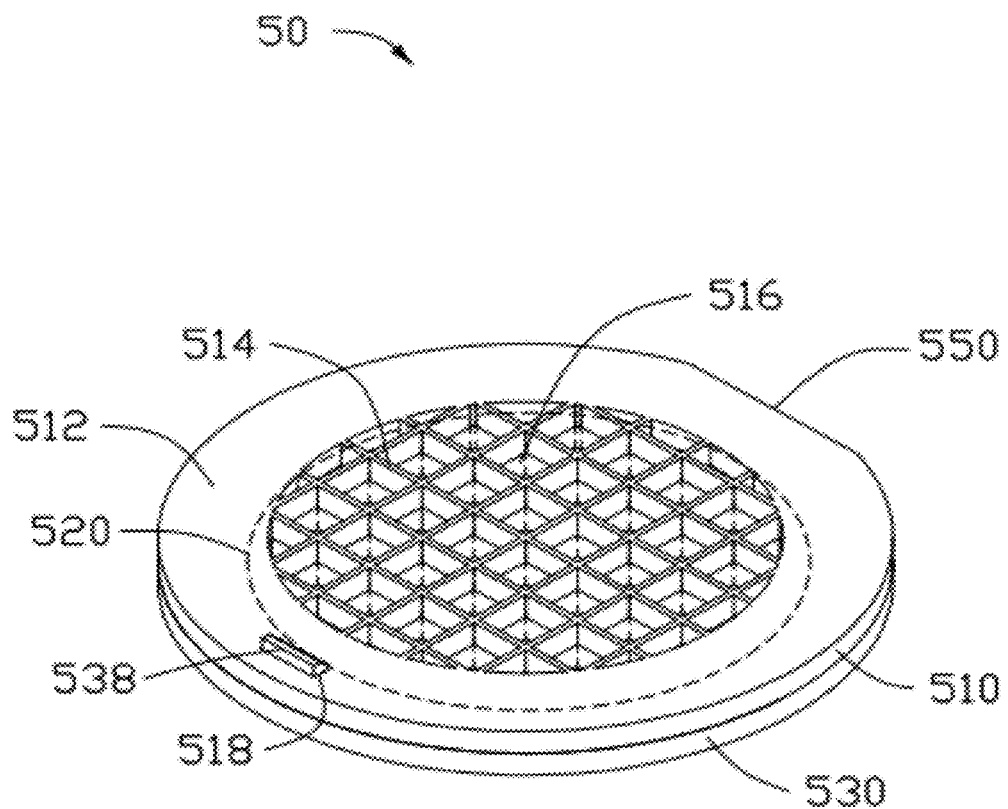
FIG. 11 is an assembled isometric view of the micro-grid of FIG. 10.

Referring to FIG. 10 and FIG. 11, still yet another embodiment of a TEM micro-grid 50 includes a carrier 510, a carbon nanotube supporter 520, and a protector 530. The carbon nanotube supporter 520 is located between the carrier 510 and the protector 530. A joint part 550 can be formed between the carrier 510 and the protector 530. In one embodiment, the micro-grid 50 can be a substantially round sheet having a diameter of about 3 mm, and a thickness in a range from about 3 μm to about 20 μm.

The carrier 510 can be a sheet-shaped structure. The carrier 510 includes a first round frame 512 and a first net 514. The first round frame 512 defines one first through opening 511 at a center. A plurality of crossed bars is formed in the first through opening 511 to divide the first through opening 511 into a plurality of first through holes 516. The crossed bars and the first through holes 516 cooperatively define the first net 514. In one embodiment, the first through opening 511 has a circular configuration. The first round frame 512 has a slit 518. The protector 530 can be a sheet-shaped structure. The protector 530 includes a second round frame 532. The second round frame 532 defines one second through opening 531 at a center. A plurality of crossed bars is formed in the second through opening 531 to divide the second through opening 531 into a plurality of second through holes 536. The crossed bars and the second through holes 536 cooperatively define a second net 534. A clasp 538 is located on the second round frame 532 and is able to engage in the slit 518.

The carrier 510 and the protector 530 are connected with each other through the joint part 550 and can be freely folded up. Specifically, the joint part 550 is formed between the first round frame 512 and the second round frame 532. Thus, the first round frame 512 connects to the second round frame 532 to form a shape similar to "8". The joint part 550 can be integrated with the carrier 510 and the protector 530. The joint part 550 can also be separated from the carrier 510 and the protector 530, such as a hinge. An inner border of the first round frame 512 and an inner border of the second round frame 532 can be superposed after the carrier 510 is folded up with the protector 530. In one embodiment, the carrier 510 and the protector 530 are superposed. When the carrier 510 and the protector 530 are folded up, the clasp 538 is engaged in the slit 518. Thus, the carbon nanotube supporter 520 is tightly fixed between the carrier 510 and the protector 530.

In one embodiment, the plurality of first through holes 516 is exactly aligned with the second through holes 536 one by one after the carrier 510 and the protector 530 are folded up. Each first through hole 516 and corresponding second through hole 536 together define an electron transmission area. The carbon nanotube supporter 520 is suspended.

The carbon nanotube supporter 520 can be the carbon nanotube structure. In one embodiment, the carbon nanotube supporter 520 is two stacked carbon nanotube films. The carbon nanotubes in one carbon nanotube film can be substantially perpendicular to carbon nanotubes in another carbon nanotube film. As such, a plurality of micropores is formed with effective diameters of about 1 nm to about 1 μm.

It is to be understood that the slit 518 and the clasp 538 are optional structures.

One embodiment of a method for making a TEM micro-grid includes the following steps:
(a) providing a carrier with a first through opening, a carbon nanotube structure, and a protector with a second through opening;
(b) applying the carbon nanotube structure on the first through opening; and
(c) stacking the protector on the carbon nanotube structure, to fix the carbon nanotube structure between the carrier and the protector.

In step (a), the carrier and the protector can be two separate structures or one integrated structure. In one embodiment, the first through opening can be divided into a plurality of first through holes or without any bars located therein. The structure of the second through opening is similar to that of the first through opening. That is, the second through opening can be divided into a plurality of second through holes or without any bars located therein. If the carrier and the protector are an integrated structure, the carbon nanotube structure can be laid over the first through opening and the second through opening simultaneously. The carbon nanotube structure can include at least one carbon nanotube film, at least one carbon nanotube wire structure, or at least one carbon nanotube network consisting of at least one carbon nanotube wire. The at least one carbon nanotube film and the carbon nanotube wire structure can be drawn from a carbon nanotube array.

The step (b) can further include a step of treating the carbon nanotube structure with an organic solvent.

The step (c) can further include a step of fixing the carrier and the protector by a mechanical method, such as soldering or clasping.

It can be understood that the method for making a TEM micro-grid can further include a step (d) of removing the carbon nanotube structure exceeding a border of the carrier to form a carbon nanotube supporter laid on the carrier.

Figure 12:
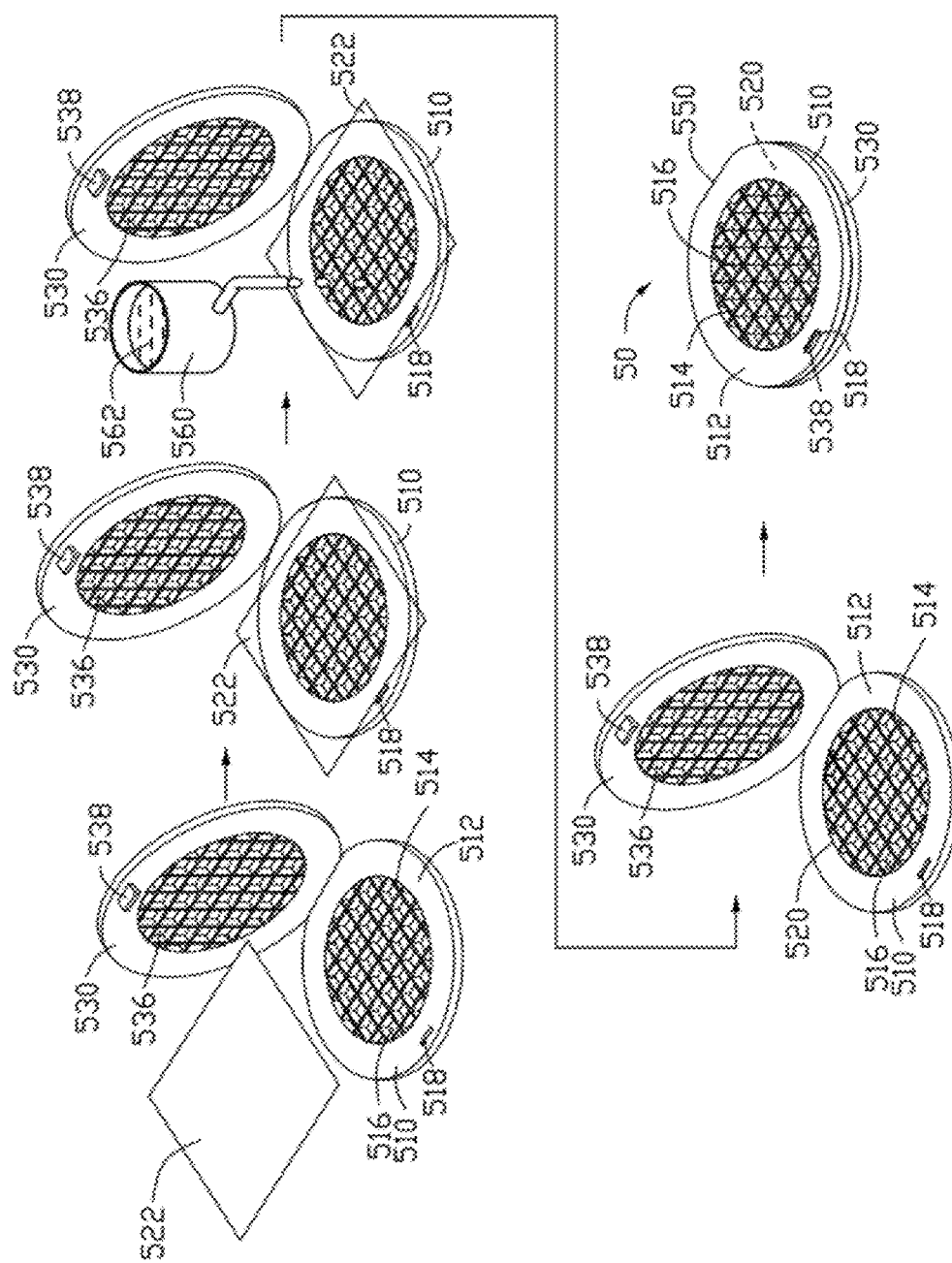
FIG. 12 illustrates one embodiment of making the micro-grid of FIG. 11.

Referring to FIG. 12, one embodiment of a method for making the micro-grid 50 includes the following step:

S110, providing the carrier 510, the protector 530, and a carbon nanotube structure 522, wherein the carrier 510 and the protector 530 are an integrated structure;

S120, applying the carbon nanotube structure 522 on the carrier 510; and

S130, stacking the protector 530 on the carrier 510 with the carbon nanotube structure 522 thereon to fix the carbon nanotube structure 522 between the carrier 510 and the protector 530.

In step S110, the carrier 510 is substantially perpendicular to the protector 530 at the joint part 550. The carbon nanotube structure 522 is two stacked carbon nanotube films. The orientation of carbon nanotubes in one carbon nanotube film is substantially perpendicular to the orientation of carbon nanotubes in another carbon nanotube film. Each carbon nanotube film can be made by the following steps.

First, a carbon nanotube array is provided. The carbon nanotube array is composed of a plurality of carbon nanotubes. The plurality of carbon nanotubes can be single-walled carbon nanotubes, double-walled nanotubes, multi-walled carbon nanotubes, or any combination thereof. In one embodiment, the plurality of carbon nanotubes comprises substantially parallel multi-walled carbon nanotubes. The carbon nanotube array is essentially free of impurities, such as carbonaceous or residual catalyst particles. The carbon nanotube array can be a super aligned carbon nanotube array. A method for making the carbon nanotube array is unrestricted, and can be by chemical vapor deposition methods or other methods.

Second, the carbon nanotube film is drawn from the carbon nanotube array. Specifically, one or more carbon nanotubes having a predetermined width can be selected from the carbon nanotube array. The carbon nanotubes are pulled out by a tool at a uniform speed to form carbon nanotube segments that are joined end to end to achieve a uniform drawn carbon nanotube film. Wherein, during the pulling process, as the initial carbon nanotube segments are drawn out, other carbon nanotube segments are also drawn out end to end due to van der Waals force between ends of adjacent segments. This process of pulling produces a substantially continuous and uniform carbon nanotube film having a predetermined width.

The carbon nanotube structure 522 can be made by the following steps of: providing a substrate with a smooth surface such as a ceramic sheet, and laying two carbon nanotube films in sequence on the substrate to form the carbon nanotube structure 522.

It is noted that because the carbon nanotubes in the super-aligned carbon nanotube array have a high purity and a high specific surface area, the carbon nanotube film is adhesive. As such, the carbon nanotube film can be adhered to the surface of the substrate directly and a plurality of carbon nanotube films can be adhered to a surface one after another.

Step S120 includes the steps of:

S121, laying the carbon nanotube structure 522 on the first net 514 of the carrier 510;

S122, treating the carbon nanotube structure 522 with an organic solvent 562; and S123, removing excess portions of the carbon nanotube structure 522 on edges of the carrier 510 to lay the carbon nanotube supporter 520 on the carrier 510.

The step S122 can be performed by the either dropping the organic solvent 562 from a dropper to soak the entire surface of the carbon nanotube structure 522, or immersing the carrier 510 with the carbon nanotube structure 522 thereon into a container having the organic solvent therein. The organic solvent is volatilizable and can be ethanol, methanol, acetone, dichloroethane, chloroform, or combinations thereof. After being soaked by the organic solvent 562, the carbon nanotube segments in the carbon nanotube structure 522 will at least partially compact/shrink into carbon nanotube bundles due to the surface tension created by the organic solvent 562. Due to the decrease of the surface via bundling, the coefficient of friction of the carbon nanotube structure 522 is reduced, but the carbon nanotube structure 522 maintains high mechanical strength and toughness. Further, due to the shrinking/compacting of the carbon nanotube segments into the carbon nanotube bundles, the substantially parallel carbon nanotube bundles are relatively distant (especially compared to the initial layout of the carbon nanotube segments) to each other in one layer and cross with the substantially parallel carbon nanotube bundles in each adjacent layer. As such, the carbon nanotube structure 522 having a plurality of micropores can thus be formed (i.e., the micropores are defined by the spacing/gaps between adjacent bundles). In one embodiment, the entire surface of the carbon nanotube structure 522 is soaked by ethanol dropped from a container 560.

In step S123, the extra portions of the carbon nanotube structure 522 are cut along the inner side of the first round frame 512 of the carrier 510 by a laser after the organic solvent 562 is volatilized. In one embodiment, a diameter of the carbon nanotube structure 522 is about 2.6 mm, which is substantially the same as the inner diameter of the first round frame 512.

It is noted that the step S123 is an optional step. If the diameter of the carbon nanotube structure 522 is smaller than the inner diameter of the first round frame 512, the step S123 is not needed. An order of the step S121, S122, S123 is not limited as abovementioned order, such as, the order of the step S122 and step (S121) can be changed, that is, the carbon nanotube structure 522 can be treated by the organic solvent firstly, then laid on the carrier 510.

In step S130, the carrier 510 and the protector 530 are folded up around the joint part 550 such that at least part of the plurality of the first through holes 516 covers at least part of the plurality of the second through holes 536. Specifically, a surface of the carrier 510 and a surface of the protector 530 form an angle at the joint part 550. The angle can be gradually reduced to 0 degrees. Thus, the protector 530 can completely cover the carrier 510. Simultaneously, the plurality of first through holes 516 is aligned with the plurality of second through holes 536 one by one. The carbon nanotube supporter 520 is suspended at each first through hole 516 and each second through hole 536.

It is to be understood that the carrier 510 and the protector 530 are folded up around the joint part 550. Thus, the protector 530 is easy to align with the carrier 510. It is much easier to align the plurality of first through holes 516 with the plurality of second through holes 536 one by one.

In addition, the step S130 further includes a step of fixing the carrier 510 and the protector 530 by a mechanical method after folding up the carrier 510 with the protector 530. Specifically, during the process of folding up the carrier 510 with the protector 530, the clasp 538 is inserted into the slit 518. The TEM micro-grid 50 is formed.

It is to be understood that the step S130 can be carried out between step S121 and step S122.

It is also to be understood that the carbon nanotube structure 522 are two stacked carbon nanotube films, the micro-grid 50 can be made by the following steps of:

laying a first carbon nanotube film on the first through holes 516;

laying a second carbon nanotube film on the second through holes 536; and folding up the protector 530 with the first carbon nanotube film thereon and the carrier 510 with the second carbon nanotube film thereon, to form the carbon nanotube structure 522 between the carrier 510 and the protector 530.

One embodiment of a method for making multiple micro-grids 50 includes the following steps of:

S210, providing a carbon nanotube structure 522, a plurality of protectors 530, and a substrate with a plurality of carriers 510 separately attached thereon, wherein each carrier 510 has a first through hole 516, and each protector 530 has a second through hole 536;

S220, applying the carbon nanotube structure 522 on the first through hole 516 of each carrier 510;

S230, stacking the plurality of carriers 510 with the carbon nanotube structure 522 thereon and the plurality of protectors 530 one by one, to locate the carbon nanotube structure 522 between the plurality of carriers 510 and the plurality of protectors 530; and S240, removing the carbon nanotube structure 522 between every two adjacent carriers 510 to form a carbon nanotube supporter 520 laid on each of the plurality of carriers 510.

In step S210, the substrate has a flat surface on which the plurality of carriers 510 is mounted. The substrate can be made of ceramic, metal, or glass. In one embodiment, the substrate is made of ceramic. Spaces between every two adjacent carriers 510 can not be too large or too small. If the spaces are too large, improving the yield of the micro-grids 50 is difficult. If the spaces are too small, the difficulty of producing the micro-grids 50 increases. In one embodiment, the spaces can be about 50 microns to about 200 microns. The plurality of micro-grids 50 is orderly arranged at the flat surface of the substrate. The number of the carriers 510 and the number of the protectors 530 are equal.

Step S240 can be executed by at least three methods: (1) moving a laser beam to irradiate the carbon nanotube structure 522 along the border of each carrier 510 to form a separated region which covers a corresponding carrier 510, whereby a plurality of carbon nanotube supporters 520 is separated from the carbon nanotube structure 522; (2) moving the laser beam to irradiate the carbon nanotube structure 522 along straight lines and rows between each two carriers 510, to cause the separation of carbon nanotube structure 522 between each two carriers 510 to form a plurality of carbon nanotube supporters 520; (3) moving the laser beam to irradiate the carbon nanotube structure 522 between every two carriers 510, to remove the carbon nanotube structure 522 between every two carriers 510.

Figure 13:
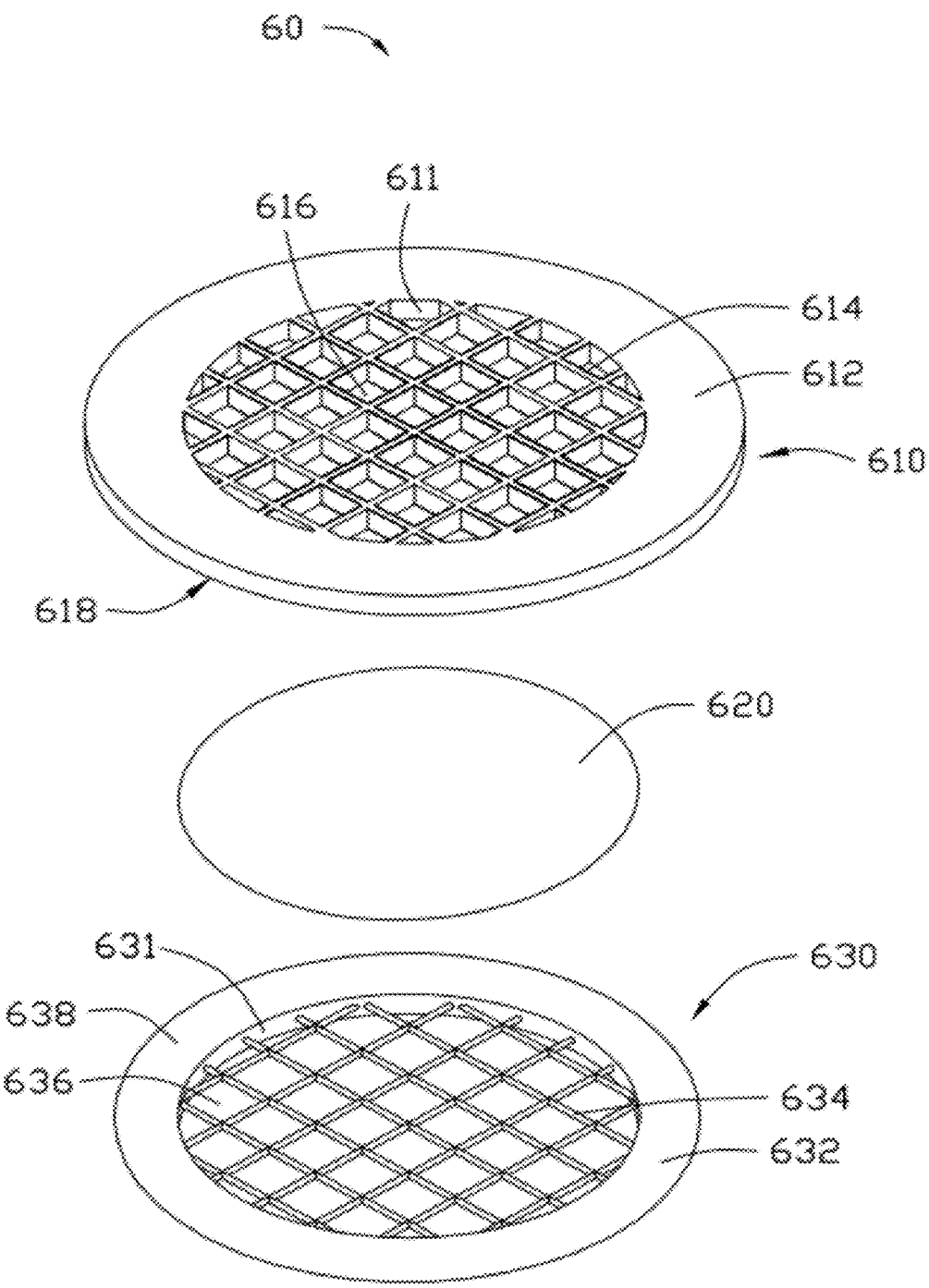
FIG. 13 is an exploded, isometric view of another embodiment of a TEM micro-grid.
Figure 14:
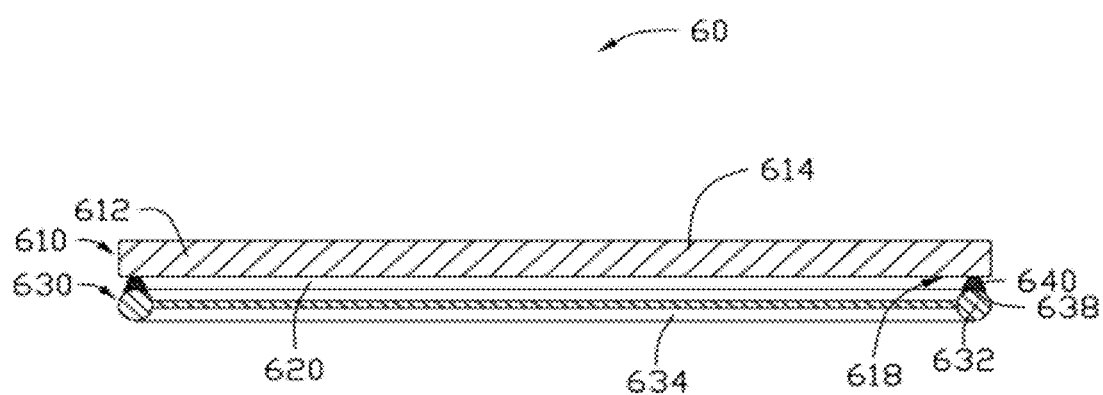
FIG. 14 is an assembled isometric view of the micro-grid of FIG. 13.

Referring to FIG. 13 and FIG. 14, one embodiment of a TEM micro-gird 60 includes a carrier 610, a carbon nanotube supporter 620, and a protector 630. The carbon nanotube supporter 620 is located between the carrier 610 and the protector 630. In one embodiment, the micro-grid 60 is a substantially round sheet, having a diameter of about 3 mm, and a thickness from about 3 μm to about 20 μm.

The carrier 610 can be a sheet-shaped structure. The carrier 610 includes a first round frame 612. The first round frame 612 defines one first through opening 611 at a center. The first through opening 611 is divided into a plurality of first through holes 616. The protector 630 can be a sheet-shaped structure. The protector 630 includes a second round frame 632. The second round frame 632 defines one second through opening 631 at a center. The second through opening 631 is divided into a plurality of second through holes 636.

The carrier 610 and the protector 630 are similar to the carrier 510 and the protector 530 except that a surface-line contact is formed between borders of the first round frame 612 and the second round frame 632, and at least one soldering element 640 is located between the carrier 610 and the protector 630. "Surface-line contact" in this disclosure can be interpreted as a plane contacting a line.

More specifically, the first round frame 612 has a substantially flat surface 618. A cross section surface of the first round frame 612 can be rectangle-shaped, semicircle-shaped, triangle-shaped, or trapezoid-shaped. The second round frame 632 has a curved surface 638. A cross section surface of the second round frame 632 can be round-shaped, semicircle-shaped, ellipse-shaped, arc-shaped, or arris-shaped. In one embodiment, the cross section surface of the first round frame 612 is rectangle-shaped, and the cross section of the second round frame 632 is round-shaped. The surface-line contact of the carrier 610 and the protector 630 makes an inner border of the second round frame 632 align with an inner border of the first round frame 612, and can easily fix the carrier 610 and the protector 630. In one embodiment, the plurality of second through holes 636 can be aligned with the plurality of first through holes 616 one by one.

It can be understood that structures of the carrier 610 and the protector 630 are not limited as mentioned above as long as the carrier 610 defining the first through opening 611 and the protector 630 defining the second through opening 631 can cause a surface-line contact.

The at least one soldering element 640 is formed by soldering the carrier 610 and the protector 630, and placed at a position where the first round frame 612 contacts the second round frame 632. The at least one soldering element 640 is located between the flat surface 618 of the first round ring 612 and the curved surface 638 of the second round ring 632 by spot welding or braze welding. The at least one soldering element 640 can be configured for fixing the carrier 610 and the protector 630, such that the carbon nanotube supporter 620 is tightly clamped between the carrier 610 and the protector 630. In one embodiment, the micro-grid 60 includes a plurality of soldering elements 640.

The carbon nanotube supporter 620 can be the carbon nanotube structure described above. In one embodiment, the carbon nanotube supporter 620 is two stacked carbon nanotube films. The orientation of carbon nanotubes in one carbon nanotube film can be substantially perpendicular to the orientation of carbon nanotubes in another carbon nanotube film. As such, a plurality of micropores with effective diameters of about 1 nm to about 1 μm is formed.

Figure 15:
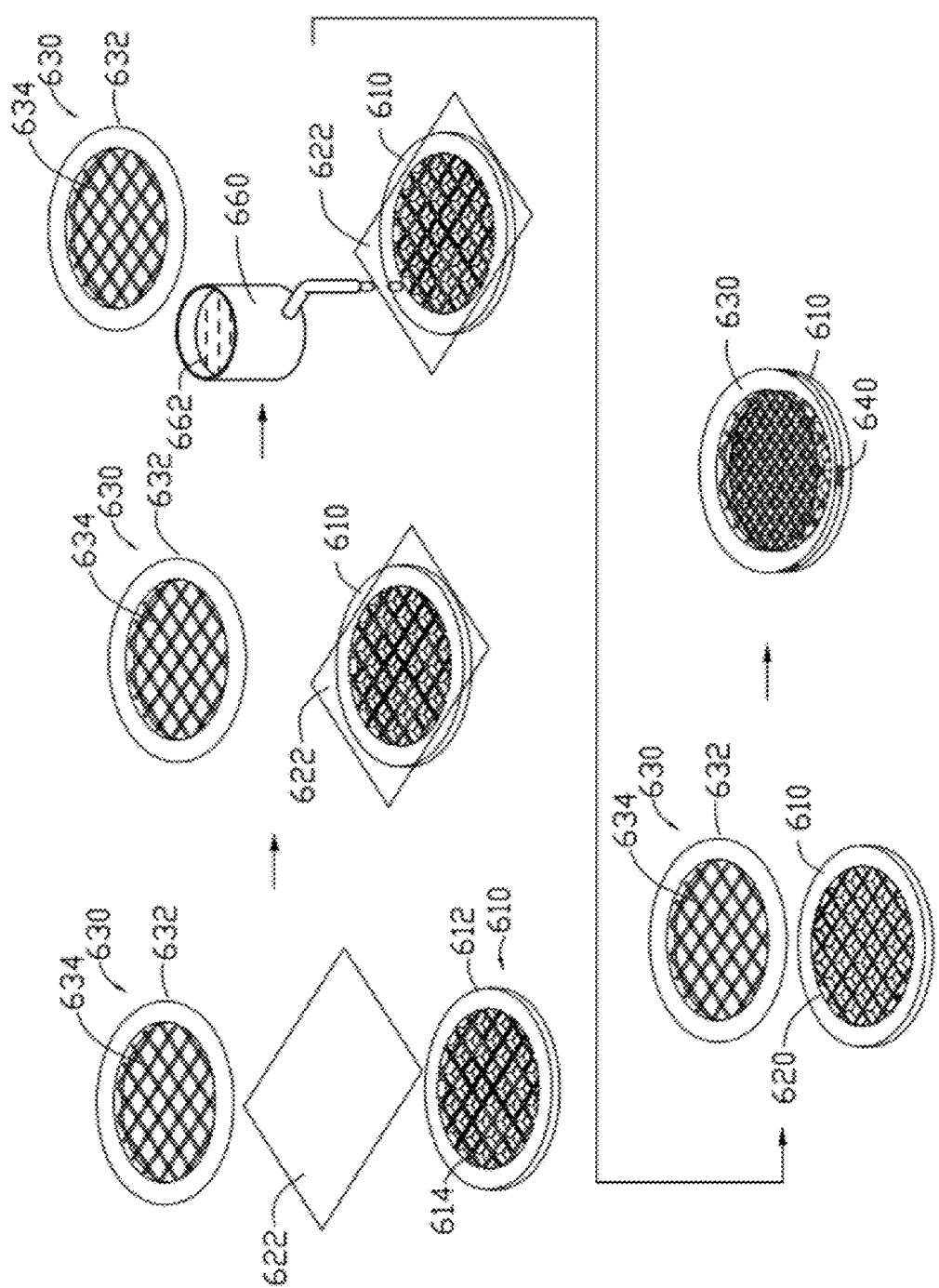
FIG. 15 illustrates one embodiment of making the micro-grid of FIG. 13.

Referring to FIG. 15, one embodiment of a method for making the micro-grid 60 includes the following steps:

S310, providing the carrier 610, the protector 630, and a carbon nanotube structure 622;

S320, stacking the protector 630, the carbon nanotube structure 622, and the carrier 610 to fix the carbon nanotube structure 622 between the carrier 610 and the protector 630; and S330, welding the carrier 610 and the protector 630.

Step (S320) includes the steps of:

S321, applying the carbon nanotube structure 622 on the flat surface 618 of the first round frame 612;

S322, treating the carbon nanotube structure 622 with an organic solvent 662 contained in a container 660;

S323, removing the carbon nanotube structure 622 exceeding the border of the carrier 610 to form a carbon nanotube supporter 620 laid on the carrier 610; and S324, applying the curved surface 638 of the protector 630 on the carrier 610 with the carbon nanotube supporter 620 thereon.

In step S324, each second through hole 636 at least partly covers the first through hole 616 corresponding to the second through hole 636. In one embodiment, the plurality of second through holes 636 completely overlaps with the plurality of first through holes 616 one by one.

Step S330 can be carried out by the following substeps of:

S3301, applying a pressure at the first round frame 612 and the second round frame 632 by a welding system, thereby forming the surface-line contact of the flat surface 618 of the first round frame 612 and the curved surface 638 of the second round frame 632; and S3302, welding the first round frame 612 and the second round frame 632 at the position where the flat surface 618 contacts the curved surface 638.

In step 53302, the at least one solder element 640 is formed. In one embodiment, the welding system is a spot welding machine. Material of the at least one solder element 640 is the same as that of the first round frame 612 and the second round frame 632.

In addition, when the carbon nanotube supporter 620 includes two stacked carbon nanotube films, the TEM micro-grid 60 can be made by the following steps of:

laying a first carbon nanotube film on the plurality of first through holes 616;

laying a second carbon nanotube film on the plurality of second through holes 636; and applying the protector 630 with the second carbon nanotube film thereon on the carrier 610 with the first carbon nanotube film thereon, to locate the carbon nanotube supporter 620 between the carrier 610 and the protector 630.

One embodiment of a method for making multiple TEM micro-grids 60 includes the following steps of:

S410, providing a plurality of carriers 610, a plurality of protectors 630, and a carbon nanotube structure 622, wherein the plurality of carriers 610 is laid on a substrate and separated from each other;

S420, applying the carbon nanotube structure 622 on the first through hole 616 of each carrier 610;

S430, stacking the plurality of carriers 610 with the carbon nanotube structure 622 thereon on the plurality of protectors 630 one by one to locate the carbon nanotube structure 622 between the plurality of carriers 610 and the plurality of protectors 630;

S440, removing the carbon nanotube supporter 622 between adjacent carriers 610 to locate a carbon nanotube supporter 620 on each of the plurality of carriers 610; and S450, welding each carrier 610 and the protector 630 corresponding to the carrier 610.

Methods for carrying out step S410, step S420, and step S440 are the same as that of step S210, step S220, and step S230 in sequence. The carrier 610 and the protector 630 can be a separated structure or an integrated structure.

Methods for executing step S430 and step S450 can be the same as that of step S324 and step S330 in sequence. The number of the carriers 610 is equal to that of the protectors 630. Each carbon nanotube supporter 620 is located between the carrier 610 and the protector 630.

According to the above descriptions, the TEM micro-grids of the present disclosure have the following advantages.

First, because the carbon nanotube supporters are secured between the first round frames and the second round frames, the TEM micro-grids can be moved using tweezers to clamp the first round frames and the second round frames. The tweezers will not contact the carbon nanotube supporters, which can prevent contaminating the carbon nanotube supporters from the tweezers.

Second, because the carbon nanotube supporters are secured between the first round frames and the second round frames, this prevents the carbon nanotube supporters from floating when the TEM micro-grids are removed. Therefore, the resolution and accuracy of a TEM adopting the TEM micro-grids can be improved. In addition, the carbon nanotube supporters are fixed between the carriers and the protectors by the slits coupled with the clasps or welding, which can further prevent the carbon nanotube structure supporters from floating when the TEM micro-grids are removed.

Third, compared to the conventional method for making TEM micro-grid, the TEM micro-grid in the present disclosure can be formed by securing a carbon nanotube structure between a carrier and a protector. The method is simple, fast, and conducive to large-scale production.

Lastly, compared to the conventional method for making TEM micro-grids, the TEM micro-grid in the present disclosure can be formed by folding up a protector with a carrier or by welding a protector on a carrier, to fix a carbon nanotube structure between the carrier and the protector. The methods can be easy to align with the protector at the carrier, especially because each second through hole can be exactly aligned with the first through hole corresponding to the second through hole.

It is to be understood that the above-described embodiment is intended to illustrate rather than limit the disclosure. Variations may be made to the embodiment without departing from the spirit of the disclosure as claimed. The above-described embodiments are intended to illustrate the scope of the disclosure and not restricted to the scope of the disclosure.

It is also to be understood that the above description and the claims drawn to a method may include some indication in reference to certain steps. However, the indication used is only to be viewed for identification purposes and not as a suggestion as to an order for the steps.

What is claimed is:

1. A method for making a transmission electron microscope micro-grid, comprising:
   (a) providing a carrier, a carbon nanotube structure, and a protector, wherein the carrier comprises a first frame, the first frame has a substantially flat surface and defines a first through opening, the protector comprises a second frame, and the second frame has a curved surface and defines a second through opening;
   (b) stacking the protector, the carbon nanotube structure, and the carrier to locate the carbon nanotube structure between the carrier and the protector, wherein the flat surface faces the curved surface, and the first through opening at least partly overlaps with the second through opening; and
   (c) welding the carrier and the protector to form the transmission electron microscope micro-grid.

2. The method of claim 1, wherein a material of the carrier is copper, nickel, molybdenum, or ceramic.

3. The method of claim 1, wherein the carbon nanotube structure comprises at least one carbon nanotube film, at least one carbon nanotube wire, or at least one carbon nanotube network.

4. The method of claim 1, wherein the carbon nanotube structure comprises a carbon nanotube film consisting of a plurality of carbon nanotubes substantially arranged along a same direction and joined end-to-end by van der Waals attractive force therebetween.

5. The method of claim 4, wherein the carbon nanotube film is created by providing a carbon nanotube array and drawing the carbon nanotube film from the carbon nanotube array.

6. The method of claim 1, wherein step (b) comprises the substeps of:
   (b1) applying the carbon nanotube structure on a surface of the carrier; and (b2) applying the protector on the carrier with the carbon nanotube structure thereon such that the second through opening at least partly covers the first through opening.

7. The method of claim 6, wherein the first through opening is divided into a plurality of first through holes, the second through opening is divided into a plurality of second through holes, the step (b2) is carried out such that the second through holes align with the first through holes one by one.

8. The method of claim 1, wherein step (b) further comprises a step of treating the carbon nanotube structure by an organic solvent.

9. The method of claim 1, wherein step (b) further comprising a step of removing the carbon nanotube structure exceeding a border of the carrier.

10. The method of claim 1, wherein a cross section surface of the first frame is rectangle-shaped, semicircle-shaped, triangle-shaped, or trapezoid-shaped.

11. The method of claim 10, wherein a cross section surface of the second frame is round-shaped, semicircle-shaped, ellipse-shaped, arc-shaped, or arris-shaped.

12. The method of claim 1, wherein the step (c) comprises the substeps of:
(c1) applying a pressure at the first frame and the second frame by a welding system, thereby forming a surface-line contact between the flat surface and the curved surface; and
(c2) welding the first frame and the second frame at a position of the surface-line contact.

13. The method of claim 1, wherein the carbon nanotube structure comprises two stacked carbon nanotube films.

14. The method of claim 13, wherein step (b) comprises the substeps of:
(b1) laying a first carbon nanotube film on the carrier;
(b2) laying a second carbon nanotube film on the protector; and
(b3) applying the protector with the second carbon nanotube film on the carrier with the first carbon nanotube film to locate the carbon nanotube structure between the first through opening and the second through opening.

15. A method for making multiple transmission electron microscope micro-grids, comprising:
(a) providing a plurality of carriers, a carbon nanotube structure, and a plurality of protectors, wherein the carriers is laid on a substrate and separated from each other, each of the carriers comprises a first frame and defines a first through opening, and each of the protectors comprises a second frame and defines a second through opening;
(b) applying the carbon nanotube structure on the first through opening of each of the carriers;
(c) stacking the protectors on the carriers with the carbon nanotube structure thereon one by one, to locate the carbon nanotube structure between the carriers and the protectors, and the flat surface faces the curved surface;
(d) removing the carbon nanotube structure between every two adjacent carriers to form a carbon nanotube supporter located on each of the carriers; and
(e) welding each of the protectors with one of the carriers corresponding to the protector to form multiple transmission electron microscope micro-grids.

16. The method of claim 15, wherein a cross section surface of the first frame is rectangle-shaped, semicircle-shaped, triangle-shaped, or trapezoid-shaped.

17. The method of claim 16, wherein a cross section surface of the second round frame is round-shaped, semicircle-shaped, ellipse-shaped, arc-shaped, or arris-shaped.

18. The method of claim 15, wherein step (d) is performed by moving a laser beam to irradiate the carbon nanotube structure along a border of each of the carriers to form a separated region which covers a corresponding carrier, whereby a plurality of carbon nanotube supporters is separated from the separated region of the carbon nanotube structure.

19. The method of claim 15, wherein step (d) is performed by moving a laser beam to irradiate the carbon nanotube structure along straight lines and straight rows between every two adjacent carriers to cause a separation of the carbon nanotube structure between every two adjacent carriers to form a plurality of carbon nanotube supporters.

20. The method of claim 15, wherein step (d) is performed by moving a laser beam to irradiate the carbon nanotube structure between every two adjacent carriers to remove the carbon nanotube structure between every two adjacent carriers.

* * * * *